US008176584B2

(12) United States Patent
Hornbach et al.

(10) Patent No.: US 8,176,584 B2

(45) Date of Patent: May 15, 2012

(54) PATIENT-SUPPORT APPARATUS WITH MOVABLE TOP

(75) Inventors: David W. Hornbach, Brookville, IN (US); Richard H. Heimbrock, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 399 days.

(21) Appl. No.: 12/535,742

(22) Filed: Aug. 5, 2009

(65) Prior Publication Data

US 2010/0050343 A1 Mar. 4, 2010

Related U.S. Application Data

(60) Provisional application No. 61/092,802, filed on Aug. 29, 2008.

(51) Int. Cl.
*A61B 6/04* (2006.01)
*A61G 13/00* (2006.01)

(52) U.S. Cl. ................................ 5/601; 5/611; 378/209

(58) Field of Classification Search .............. 5/600, 601, 5/611; 378/209; 108/143, 145, 147
See application file for complete search history.

(56) References Cited

U.S. PATENT DOCUMENTS 1,216,633 A 2/1917 Wantz
2,605,151 A 7/1952 Shampaine
2,707,137 A 4/1955 Hollstein
2,872,584 A 2/1959 Schiring et al.
2,906,880 A 9/1959 Stava et al.
3,043,953 A 7/1962 Craig et al.
3,131,301 A 4/1964 Barrett et al.
3,158,742 A 11/1964 Morel et al.
3,222,518 A 12/1965 Agel
3,281,141 A 10/1966 Smiley et al.
3,302,022 A 1/1967 Brenner et al.
3,397,411 A 8/1968 Rossi
3,473,024 A 10/1969 Feiertag
3,588,500 A 6/1971 Koerner
3,757,129 A 9/1973 Hogan
3,814,414 A 6/1974 Chapa
3,818,516 A 6/1974 Hopper et al.
3,840,221 A 10/1974 Hogan (Continued)

FOREIGN PATENT DOCUMENTS

DE 299 18 805 U1 2/2000

(Continued)

OTHER PUBLICATIONS

European search report from EP 09 25 2082 dated Jul. 30, 2010 (6 pages).

*Primary Examiner* — Michael Trettel

(74) *Attorney, Agent, or Firm* — Barnes & Thornburg LLP

(57) ABSTRACT

A patient-support apparatus includes frame and a lift arm. The frame includes a base frame and an upper frame. The lift arm has a first end coupled to the upper frame and a second end spaced apart from the first end and coupled to the base frame. In this embodiment, the lift arm is configured to move the frame in a generally vertical direction while the lift arm rotates with respect to the frame. The apparatus is configured to allow the first end of the lift arm to translate along the upper frame while the second end rotates about an axis that is fixed relative to the base frame. Other embodiments are also disclosed.

23 Claims, 10 Drawing Sheets

U.S. PATENT DOCUMENTS

| | | | |
|---|---|---|---|
| 3,845,947 | A | 11/1974 | Lee |
| 3,868,103 | A | 2/1975 | Pageot et al. |
| 3,980,288 | A | 9/1976 | Mitchell et al. |
| 4,013,019 | A | 3/1977 | Horsey |
| 4,037,871 | A | 7/1977 | Bourgraf et al. |
| 4,061,324 | A | 12/1977 | Kvaerna et al. |
| 4,145,612 | A | 3/1979 | Cooper |
| 4,190,043 | A | 2/1980 | Thompson |
| 4,195,829 | A | 4/1980 | Reser |
| 4,326,613 | A | 4/1982 | Houlberg |
| 4,327,596 | A | 5/1982 | Simon |
| 4,671,728 | A | 6/1987 | Clark et al. |
| 4,700,938 | A | 10/1987 | Chambron |
| 4,769,584 | A | 9/1988 | Irigoyen et al. |
| 4,773,637 | A | 9/1988 | Jarin |
| 4,926,457 | A | 5/1990 | Poehner et al. |
| 4,944,500 | A | 7/1990 | Mueller et al. |
| 4,956,592 | A | 9/1990 | Schulte et al. |
| 4,984,774 | A | 1/1991 | Zupancic et al. |
| 4,989,848 | A | 2/1991 | Monroe |
| 5,054,141 | A | 10/1991 | Foster et al. |
| 5,131,103 | A | 7/1992 | Thomas et al. |
| 5,181,288 | A | 1/1993 | Heaton et al. |
| 5,220,698 | A | 6/1993 | Hannant |
| 5,230,112 | A | 7/1993 | Harrawood et al. |
| 5,441,129 | A | 8/1995 | Porter et al. |
| 5,469,588 | A | 11/1995 | DiMatteo et al. |
| 5,490,297 | A | 2/1996 | Bradcovich et al. |
| 5,659,909 | A | 8/1997 | Pfeuffer et al. |
| 5,832,056 | A | 11/1998 | Mochitate et al. |
| 5,996,149 | A | 12/1999 | Heimbrock et al. |
| 6,038,718 | A | 3/2000 | Pennington et al. |
| 6,202,230 | B1 | 3/2001 | Borders |
| 6,226,821 | B1 | 5/2001 | Heimbrock et al. |
| 6,240,582 | B1 | 6/2001 | Reinke |
| 6,266,831 | B1 | 7/2001 | Heimbrock |
| 6,282,738 | B1 | 9/2001 | Heimbrock et al. |
| 6,615,429 | B2 | 9/2003 | Weil et al. |
| 6,615,430 | B2 | 9/2003 | Heimbrock |
| 6,782,571 | B1 | 8/2004 | Josephson et al. |
| 6,843,182 | B2 | 1/2005 | Torcheboeuf |
| 7,024,710 | B2 * | 4/2006 | Izuhara .............................. 5/601 |
| 7,131,769 | B2 | 11/2006 | Vezina |
| 7,150,056 | B2 | 12/2006 | Lemire |
| 7,177,393 | B2 | 2/2007 | Kanemitsu |
| 2002/0138904 | A1 | 10/2002 | Wong |
| 2004/0141591 | A1 | 7/2004 | Izuhara |
| 2004/0200001 | A1 | 10/2004 | Stolze et al. |
| 2006/0277683 | A1 | 12/2006 | Lamire et al. |
| 2007/0143921 | A1 | 6/2007 | Hiyama |

FOREIGN PATENT DOCUMENTS

| | | | |
|---|---|---|---|
| DE | 10 2004 013 585 | B4 | 4/2007 |
| EP | 0 522 730 | A1 | 1/1993 |
| EP | 0 650 696 | A1 | 5/1995 |
| EP | 0 923 922 | A2 | 6/1999 |
| FR | 1.485.643 A 61 | g | 6/1967 |
| GB | 1 466 080 | | 3/1977 |
| GB | 1 554 115 | | 10/1979 |
| JP | 63-302089 | | 8/1988 |
| WO | WO 01/08621 | | 2/2001 |
| WO | 2006/063449 | A1 | 6/2006 |
| WO | WO 2006/063449 | | 6/2006 |
| WO | WO 2007/069912 | | 6/2007 |

* cited by examiner

PATIENT-SUPPORT APPARATUS WITH MOVABLE TOP

This application claims the benefit, under 35 U.S.C. §119 (e), of U.S. Provisional Patent Application No. 61/092,802 which was filed Aug. 29, 2008 and which is hereby expressly incorporated by reference herein.

BACKGROUND

The present disclosure is related to patient-support apparatuses. More specifically, in one embodiment a patient-support apparatus is provided with a sliding top for use in combination with diagnostic or therapy devices.

The care that hospitals provide patients often requires that the hospital transfer a patient between various patient-support apparatuses. However, the transfer of a patient between patient-support apparatuses may be difficult and may create discomfort, and even risk of injury, for the caregiver or the patient.

This transfer can be required because certain devices, such as C-arm X-Ray devices, for example may require placing a portion of the device above the patient and other portions of the device below a patient. However, patient-support apparatuses, (such as hospital beds and stretchers), having a lift mechanism may obstruct the placement of portions of the device above and below a patient's body.

Accordingly, improvements to patient-support apparatuses are desired.

SUMMARY

The present disclosure relates to one or more of the features recited in the appended claims and/or the following features which, alone or in any combination, may comprise patentable subject matter:

A patient-support apparatus for use in a hospital or other clinical setting may have a base and a frame. The frame may have a head end and a foot end spaced apart from the head end in a longitudinal direction. The apparatus may also have a first lift arm coupled to the base and to the frame. The first lift arm may be pivotable relative to the base to raise and lower at least a portion of the frame relative to the base. The apparatus may also have a securing assembly including a latch. The securing assembly may be configurable into a locked configuration or an unlocked configuration. When the securing assembly is in the unlocked configuration, the frame may be manually positionable relative to the base in the longitudinal direction. Alternatively, when the securing assembly is in the locked configuration, the frame may be prevented from moving in the longitudinal direction relative to the base.

The first lift arm may be coupled to the frame at a first end which may have a roller. The first end of the first lift arm may move along the frame when the frame is raised and lowered relative to the base. The securing assembly may include a link rotatably coupled to the lift arm. Also, the frame may include a series of catches engaging the latch when the securing assembly is in the locked configuration.

The apparatus may have a second lift arm coupled to the base and the frame. The second lift arm may be pivotable relative to the base to raise and lower at least a portion of the frame relative to the base. The second lift arm may also be coupled to the frame at a first end. The first end of the second lift arm may move along the frame when the frame is raised relative to the base. More specifically, the first lift arm may be pivotable relative to the base to raise and lower the head end of the frame and the second lift arm may be pivotable relative to the base to raise and lower the foot end of the frame. The securing assembly may be in a locked configuration during raising and lowering of the frame relative to the base.

The frame may include a right rail member having a groove configured to slideably engage the first lift arm roller. Also, the frame may be coupled to a radiolucent support deck.

The frame may also include a right rail member and a left rail member. The securing assembly may have a left latch and a right latch. When the securing assembly is in a locked configuration, the left latch may lockably engage the left rail member and the right latch may lockably engage the right rail member. When the securing assembly is in an unlocked configuration, the left latch may slidably engage the left rail member and the right latch may slidably engage the right rail member. The apparatus may include a spring biasing the securing assembly toward a locked configuration.

The right rail member may include catches each of which is configured to lockably engage the right latch when the right latch is aligned with a corresponding catch. Similarly, the left rail member may include catches each of which is configured to lockably engage the left latch when the left latch is aligned with a corresponding catch. The left rail catches and right rail catches may be configured to lockably engage both the left latch and right latch at predetermined longitudinal positions of the frame in relation to the base. The left latch may have a left release portion configured to release the lockable engagement of both the left latch with the left rail member and the right latch with the right rail member. Similarly, the right latch may include a right release portion configured to release the lockable engagement of both the left latch with the left rail member and the right latch with the right rail member.

The securing assembly may also include a bias rod coupled to both the left latch and the right latch. The bias rod is acted upon by at least one spring to bias both the left latch and the right latch to a locked configuration. The bias rod may include a left bend portion and a right bend portion. The securing assembly may also include rollers configured to engage opposing outer surfaces of the right rail member and opposing outer surfaces of the left rail member.

According to this disclosure, the apparatus may comprise a base, a frame, and a securing assembly. The frame may have a head end, a foot end spaced apart from the head end in a longitudinal direction, and a side rail member including a complementary pair of stop tab catches. The securing assembly may include a latch. The latch may comprise a roller configured to engage a stop tab catch, and a handle. The frame may be positionable relative to the base in the longitudinal direction when the roller is disengaged from the at least one stop tab catch.

The latch may further comprise a spring configured to bias the roller to contact the side rail. Additionally, when actuated, the handle may be configured to overcome the bias of a spring that biases the roller toward contact with the side rail member.

The complementary pair of stop tab catches may comprise a first stop tab joined at a first end to the side rail and including a second end spaced apart from the side rail forming an acute included angle with the side rail. The complementary pair of stop tab catches may also comprise a second stop tab joined at a first end to the side rail and including a second end spaced apart from the side rail forming an acute angle with the side rail. The second end of the first tab may be spaced apart from the second end of the second tab a first distance. Also, the first end of the first tab may be spaced apart from the first end of the second tab a second distance. The first distance may be smaller than the second distance.

When the securing assembly is in a locked configuration, the first distance between the second end of the first tab and the second end of the second tab may allow the roller to engage both the second end of the first tab and the second end of the second tab.

According to another aspect of the present disclosure, a patient-support apparatus may have a frame that defines a head end, a foot end, and two sides laterally spaced apart. The foot end may be longitudinally spaced apart from the head end. The patient-support also may utilize a lift arm that includes a first end coupled to the frame and a second end spaced apart from the first end. The lift arm may be configured to move the frame in a generally vertical direction during rotation of the lift arm. The apparatus may be configured to allow the first end of the lift arm to translate along the frame while the lift arm rotates relative to the base frame.

According to this disclosure, a patient-support apparatus may have a base and a frame that defines a head end, a foot end spaced apart from the foot end in a longitudinal direction, a left side and a right side spaced apart from the left side in a lateral direction. The left and right sides extend between the head end and foot end. The patient-support apparatus also may have a lift arm pivotably coupled to the base and the frame. The lift arm may be configured to move at least a portion of the frame relative to at least a portion of the base in a generally vertical direction. The patient-support apparatus also may include a securing assembly that is configurable into a locked configuration and an unlocked configuration. The frame may be positionable relative to the base in the longitudinal direction when the securing assembly is in the unlocked configuration. The frame may be in a generally fixed longitudinal position relative to the base when the securing assembly is in the locked configuration.

According to a further aspect of the present disclosure, a patient-support apparatus may have a lift-arm assembly configured to move at least a portion of the frame relative to at least a portion of the base generally in the vertical direction. The lift arm assembly may include at least one lift arm having a first end coupled to the frame for pivoting movement about a first lateral axis and a second end coupled to the base for pivoting movement about a second lateral axis. The lift arm may be configured such that the first lateral axis translates in a generally longitudinal direction with respect to the frame. The patient-support apparatus also may have a lock that includes at least one link coupled to the at least one lift arm for pivoting movement about a third lateral axis. The lock may be configured to engage the frame. At least a portion of the at least one link may rotate with respect to the frame about a fourth lateral axis. The lock may be configured to include a locked configuration and an unlocked configuration such that while in the locked configuration the fourth lateral axis remains in a fixed longitudinal position with respect to the frame and while in the unlocked configuration the fourth lateral axis is translatable in a generally longitudinal direction with respect to the frame.

According to yet another aspect of the present disclosure, a patient-support apparatus may have a lift arm slidably coupled to the frame at a first location, and a link coupling the arm to the frame at a second location. The link may be configured to be locked with the frame such that raising or lowering the frame increases the distance between the first and second locations. The link may be configured to be unlocked relative to the frame to allow longitudinal sliding of the frame with respect to the lift arm while maintaining the same distance between the first and second locations.

According to still a further aspect of the present disclosure, a patient-support apparatus utilizing a frame defining a head end, a foot end longitudinally spaced apart from the head end, and two sides laterally spaced apart. The patient-support apparatus may also have a lift arm. The apparatus may be moved between a locked condition and an unlocked condition. The apparatus may be configured to allow the lift arm to translate along the frame in a generally longitudinal direction when the apparatus is in the unlocked condition. The lift arm may be configured to translate along the frame and simultaneously lift the frame when the apparatus is in the locked condition.

Additional features alone or in combination with any other feature(s), including those listed above, those listed in the claims, and those described in detail below, may comprise patentable subject matter. Other such features and other variations will become apparent to those skilled in the art upon consideration of the following detailed description of illustrative embodiments, which exemplifies the best mode of carrying out the disclosure as presently perceived.

BRIEF DESCRIPTION OF THE DRAWINGS

The detailed description particularly refers to the accompanying figures in which.

DETAILED DESCRIPTION OF THE ILLUSTRATIVE EMBODIMENTS

The present disclosure relates to a patient-support apparatus having an upper frame movable in a longitudinal direction such as by sliding, for example. The term sliding in the present disclosure is intended to cover pure sliding and movement of an element along rolling elements, such as rollers, balls, pins, and the like. The movement allows for diagnostic equipment or other equipment to be more easily placed relative to the patient. In one embodiment, a securing assembly secures the upper frame when in a locked position and, when in the unlocked position, allows for longitudinal movement of the upper frame relative to a base frame and relative to a lift assembly.

Figure 1:
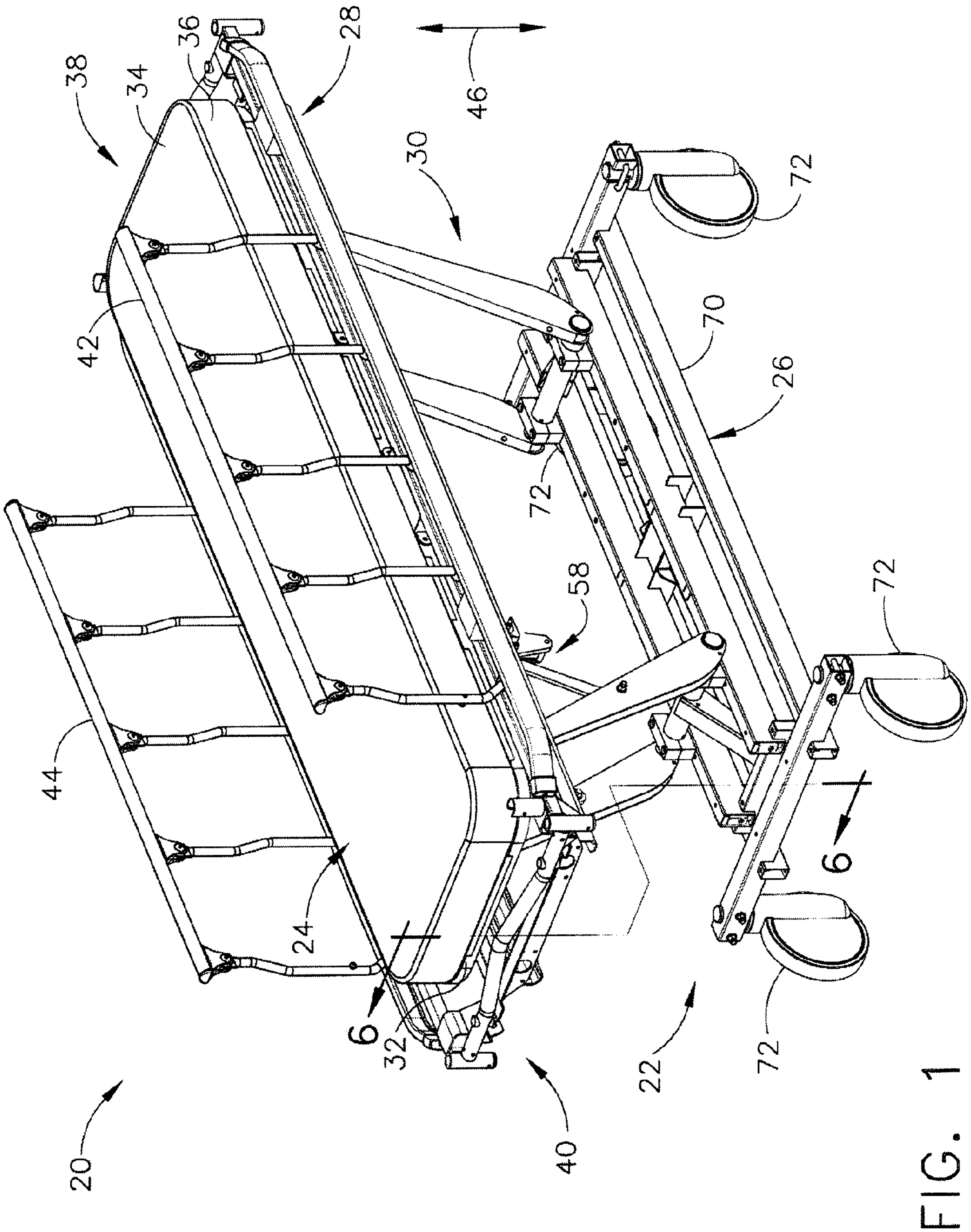
FIG. 1 is a perspective view of a patient-support apparatus in accordance with one illustrative embodiment which includes a stretcher frame.

One exemplary patient-support apparatus 20, shown in FIG. 1, is a stretcher frame 22. Stretcher frame 22 is shown illustratively supporting a support surface 24. Stretcher frame 22 includes a foot end, such as foot end 38 positioned at the upper right side of FIG. 1, and a head end, such as head end 40 at the lower left side of FIG. 1. Illustrative stretcher frame 22 has a base 26 and an upper frame 28 coupled to the base 26 by a lift mechanism 30 which is movable to raise and lower upper frame 28 relative to base 26 along as indicated in FIG. 1 by a double headed arrow 46. Stretcher frame 22 may further include a bed controller (not shown) operatively coupled to the lift mechanism 30 to control vertical movement of upper frame 28.

Support surface 24 supported by patient-support apparatus 20 may include a top surface 34, a bottom surface (not shown), and a perimeter surface 36. The bottom surface of support surface 24 is generally parallel to top surface 34. Stretcher frame 22 may include a support deck 32 that engages the bottom surface of support surface 24. A patient may occupy patient-support apparatus 20 in a supine position on top surface 34 of support surface 24, for example.

Figure 2:
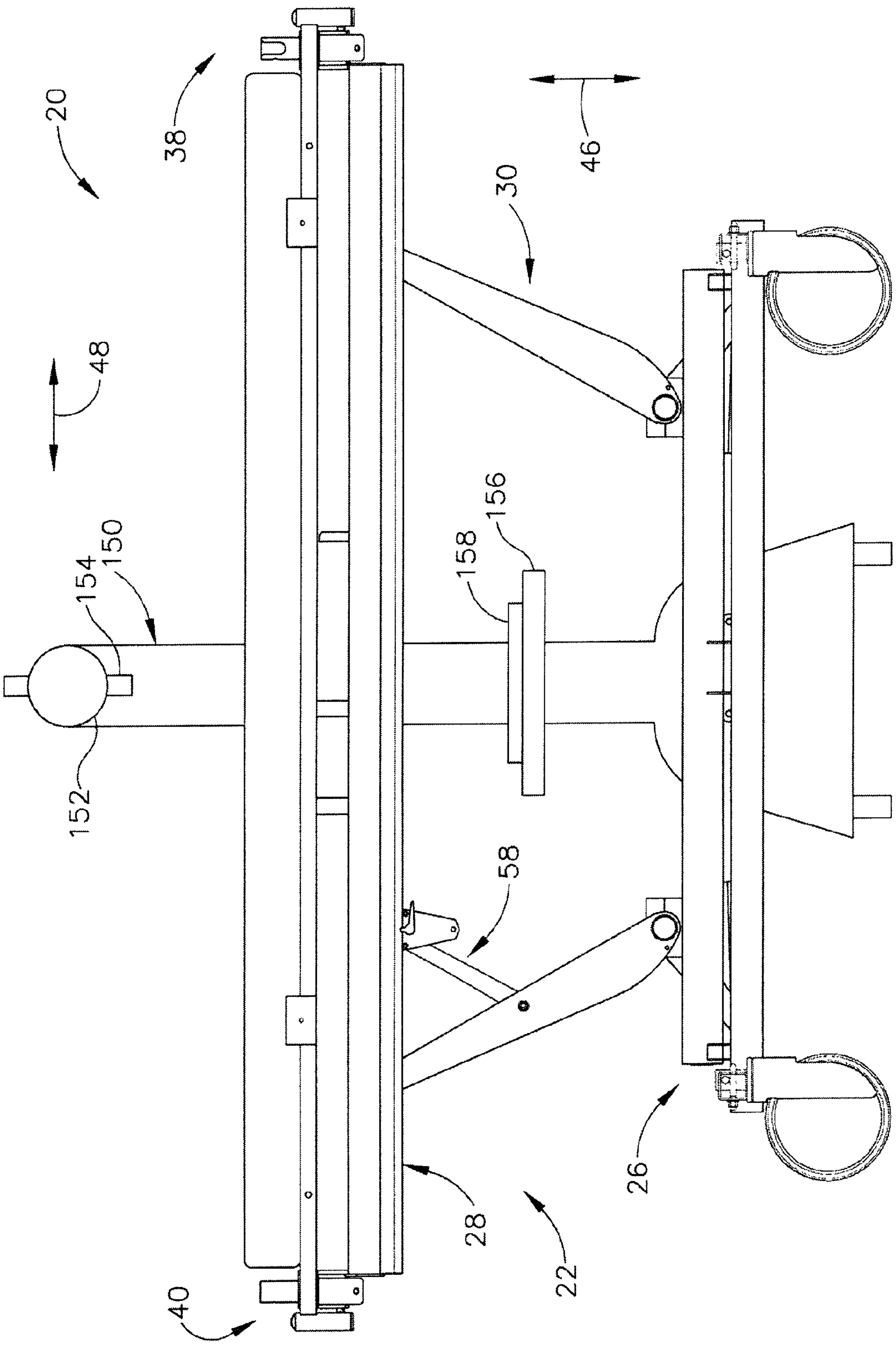
FIG. 2 is a side elevation view of the embodiment of FIG. 1 with the siderails not shown, and an illustrative diagnostic device positioned adjacent therewith, the stretcher frame shown with a securing mechanism in a secured position and an upper frame in a longitudinally fixed position with respect to a base frame.

Upper frame 28 is illustratively shown in FIG. 2 as positioned generally centered with the base 26 with lift mechanism 30 extending therebetween. As lift mechanism 30 moves along axis 46, the longitudinal position of upper frame 28 relative to base 26 may remain generally the same throughout the vertical movement.

Figure 3:
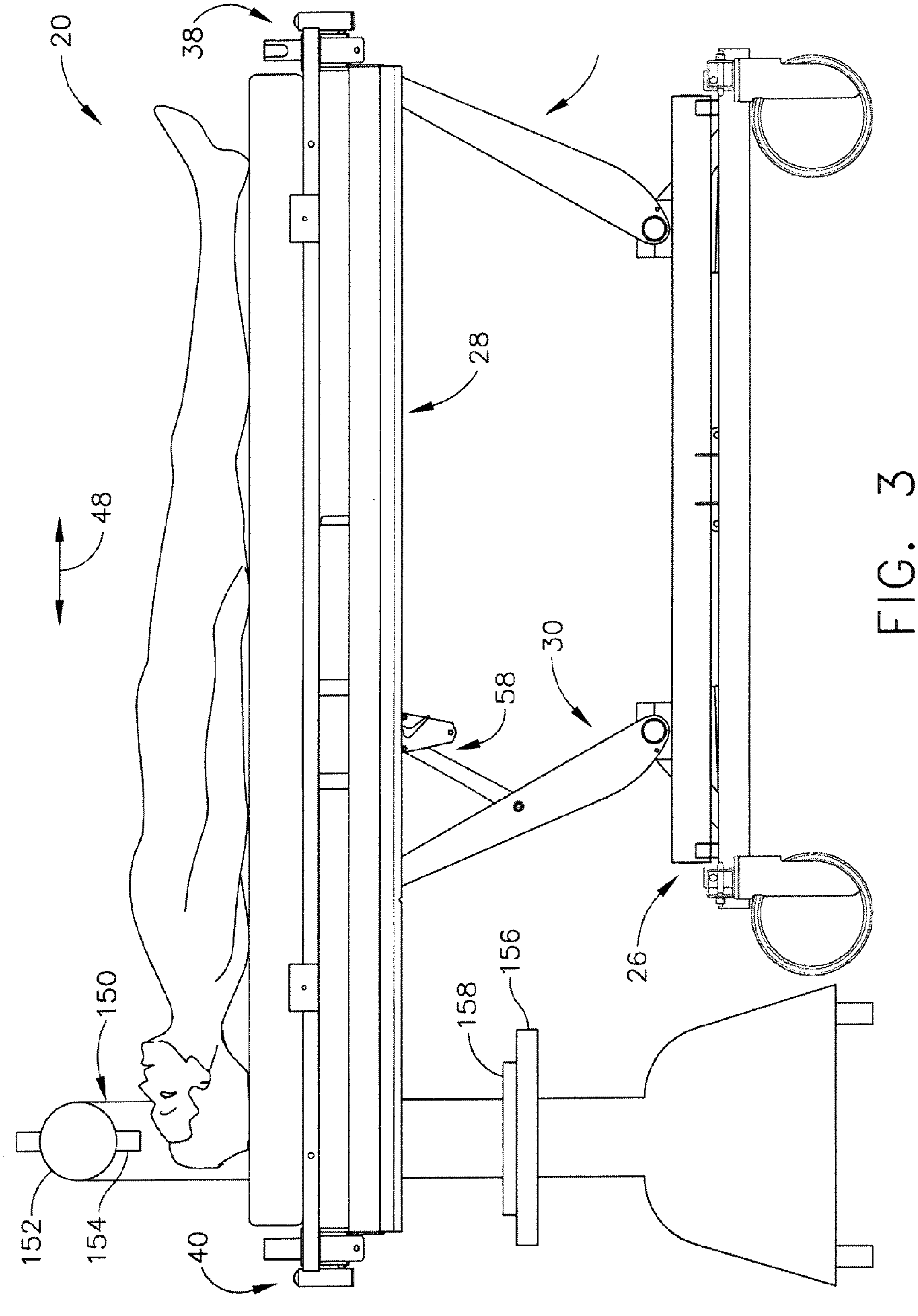
FIG. 3 is a side elevation view of the patient-support apparatus of FIG. 1 with the securing mechanism in a released position and the upper frame longitudinally moved in a head-end direction to position a patient's head at a location suitable for imaging.
Figure 4:
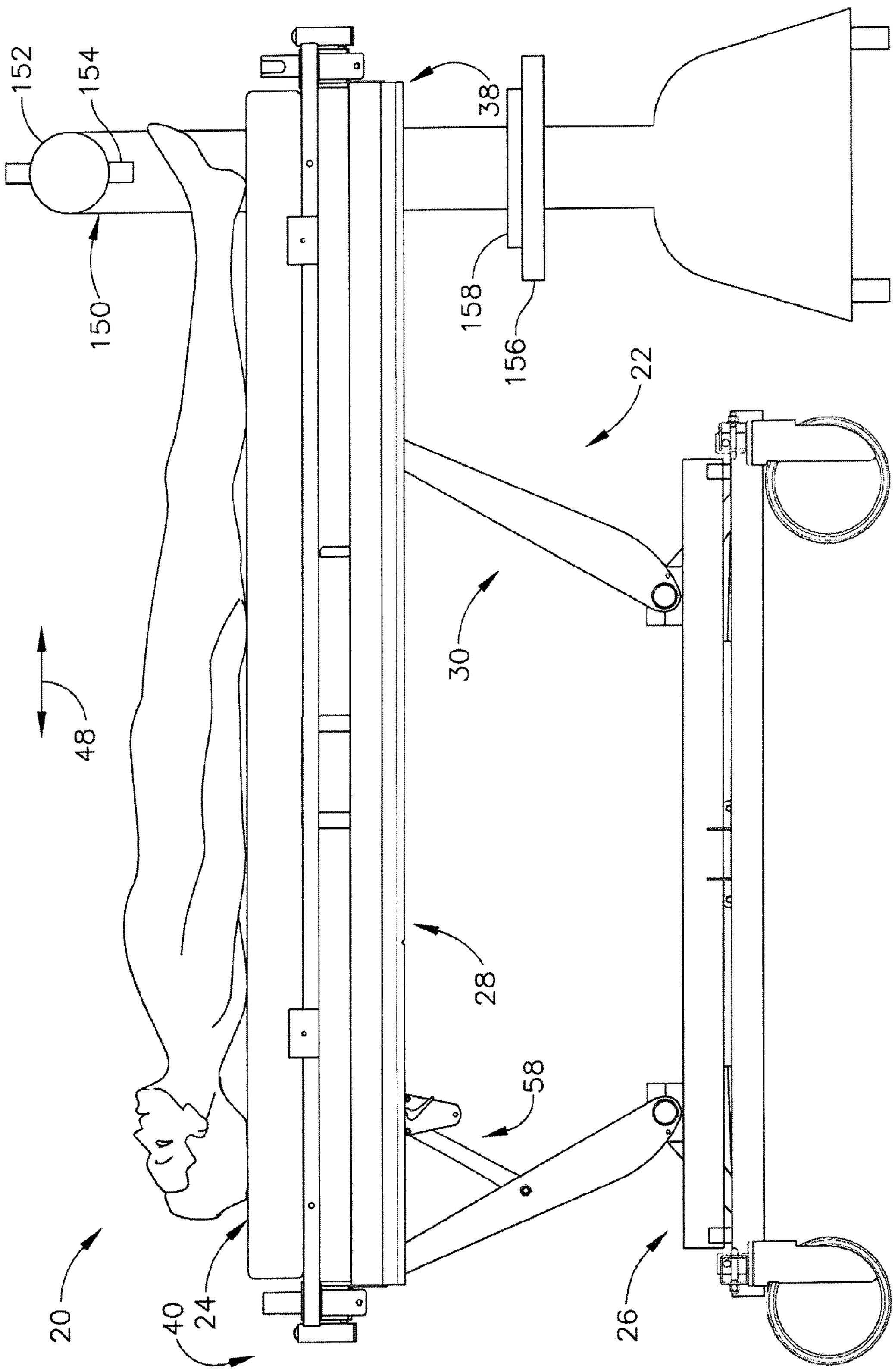
FIG. 4 is a side elevation view of the patient-support apparatus of FIG. 1 with the securing mechanism in a released position and the upper frame longitudinally moved in the foot-end direction to position the patient's feet at a location suitable for imaging.

Lift mechanism 30 of patient-support apparatus 20 can be slidably coupled to upper frame 28 allowing movement along a longitudinal axis 48, such as seen in FIGS. 3, 4. The head end 40 of stretcher frame 22 may be moved longitudinally away from base 26. Likewise the foot end 38 of stretcher frame 22 may be moved longitudinally away from base 26.

Additionally, stretcher frame 22 can include a lock, such as securing assembly 58, coupling upper frame 28 to lift mechanism 30. The lock may also be configurable into a locked configuration and unlocked configuration. The lock, such as, for example, securing assembly 58, may retain a longitudinal position of upper frame 28 with respect to base 26 when in a locked position, or secured position, as shown in FIG. 2. The lock, such as, for example, securing assembly 58, may be placed into an unlocked position, or released position, thus allowing upper frame 28 to move longitudinally with respect to base 26, as shown in FIGS. 3, 4.

A caregiver may place a patient on patient-support apparatus 20 for use in combination with a diagnostic or therapy device. For example, a fluoroscopic imaging machine 150 having a C-arm 152 with a beam generator 154 can be placed above upper frame 28 and a tray 156 can be placed beneath upper frame 28, as illustratively shown in FIGS. 2-4. Tray 156 supports a film cassette 158 that captures fluoroscopic images of the portion of the patient supported thereabove.

While the patient-support apparatus in the present embodiment is illustratively shown as stretcher frame 22, a patient-support apparatus may also include other apparatus for supporting a patient. For example, a patient-support apparatus may comprise beds of varying types, such as, for example, birthing beds, hospital beds, and bariatric beds, and tables of varying types, such as operating room tables, diagnostic tables, and examination tables. Additionally, while not shown, a patient-support apparatus may also include apparatuses with features not shown, such as, for example, therapy features, patient positioning features, patient handling features, and equipment interface features.

Upper frame 28 is shown in a head-end position in FIG. 3 and upper frame 28 is shown in a foot-end position in FIG. 4. By positioning securing assembly 58 in a released position, upper frame 28 may move between the head-end position and the foot-end position, whereby C-arm 152 is able to be positioned to take images of portions of the patient that would otherwise be inaccessible due to the obstruction lift mechanism 30 may cause. Accordingly, upper frame 28 is movable between a head-end position to a foot-end position, which provides horizontal and vertical clearance (relative to the floor) to allow the C-arm 152 to be positioned in the open space provided.

Stretcher frame 22 is illustratively shown in FIG. 1 to include a left siderail 42 and a right siderail 44 coupled to upper frame 28. Siderails 42, 44 are movable between a barrier position as shown in FIG. 1 and a lowered position wherein the siderails 42 and 44 are below top surface 34 of support surface 24. Siderails 42 and 44 may deter patient egress, support patient and caregiver equipment interfaces, provide physical support for the patient or maneuvering of the patient-support apparatus 10. While patient-support apparatus 20 is shown in the illustrative embodiment of FIG. 1 to include two siderails, in other embodiments a patient-support apparatus includes no siderails on one or both the sides or has one or more siderails on either side. FIGS. 2-7 are illustratively shown without siderails 42, 44. Additionally, while not shown, stretcher frame 22 may include a head board and a foot board coupled to upper frame 28 at head end 40 and foot end 38, respectively.

Base 26 of stretcher frame 22 may include a lower frame 70 which in this embodiment is pivotably coupled to four casters 72 as shown in FIG. 1. A patient-support apparatus may include wheel assemblies, such as casters 72, to allow mobility of patient-support apparatus 20. It is within the scope of the present disclosure for a patient-support apparatus to alternatively include one or more supports configured to engage a floor and provide a stationary patient-support apparatus.

Figure 5:
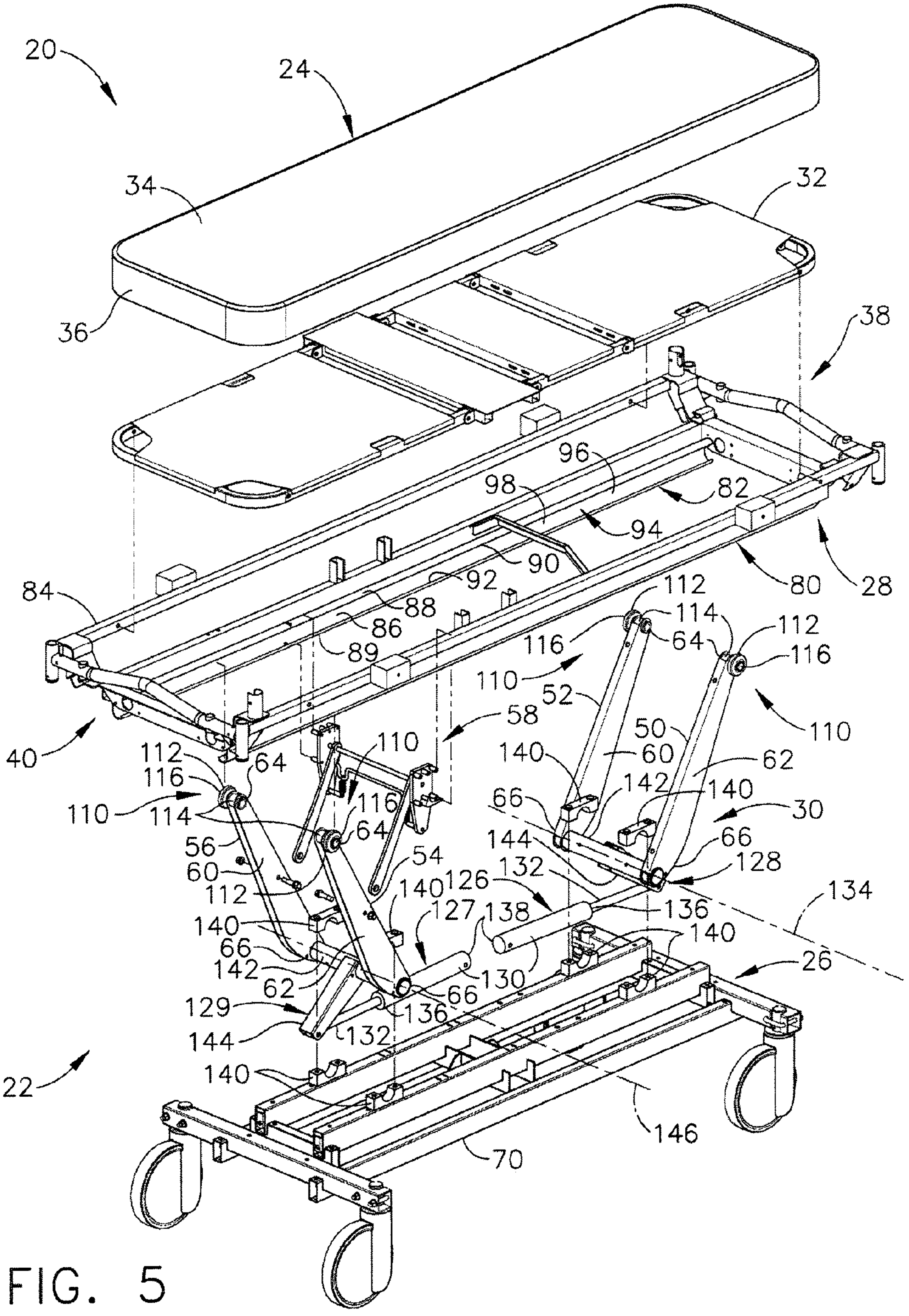
FIG. 5 is an exploded perspective view of the patient-support apparatus of FIG. 1.

In this illustrative embodiment, upper frame 28 includes a support frame 84, a right rail member 80, and a left rail member 82, as best seen in FIG. 5. Support frame 84 is coupled to support deck 32 of upper frame 28. Configuring support deck 32 to pivotably couple to support frame 84 can be accomplished in a variety of ways, such as those apparent to one skilled in the art or later to be developed. Movement of support deck 32 with respect to support frame 84 may be provided with a motion drive such as a pneumatic drive, an electric drive, a hydraulic drive, manual adjustment, or any equivalent or combination thereof. It is within the scope of the present disclosure for at least a portion of support deck 32 to be constructed of a material, such as, for example, radiolucent material, conducive to allowing diagnostic imaging equipment to operate while a patient is supported by support deck 32.

While right rail member 80 is attached to the right side of support frame 84 and left rail member 82 is attached to the left side of support frame 84, rail members 80 and 82 have the same structure and features as shown in FIG. 5. Right rail member 80 and left rail member 82 each have an inward side 86 facing toward the lateral center of the patient-support apparatus 20, an outward side (not shown) facing opposite inward side 86, a top side 88 and a bottom side 89. The outward sides of rail members 80 and 82 are attached to support frame 84, as best seen in FIG. 5. Inward side 86 is formed to include two edges 90, 92 extending from the head end of rail members 80 and 82 to the foot end of rail members 80 and 82. Edges 90, 92 form an opening 94 that, in cooperation with a groove surface 96, extends between edges 90, 92 to define a groove 98. Many other configurations are possible though in other embodiments.

Lift mechanism 30 of stretcher frame 22 illustratively includes two motion drives 126, 127, two motion couplers 128, 129, and four lift arms 50, 52, 54 and 56. Lift arms 50-56 stretch between base 26 and upper frame 28, as seen best in FIG. 5. The foot end 38 of upper frame 28 is raised and lowered with respect to base 26 as lift arms 50 and 52 move, and the head end 40 of upper frame 28 is raised and lowered with respect to base 26 as lift arms 54 and 56 move. Lift arms 50-56 each have an inward side 60 facing toward the lateral center of the patient-support apparatus 20 and an outward side 62 facing opposite inward side 60. Additionally, lift arms 50-56 have an upper end 64 and a lower end 66.

It is within the scope of the present disclosure for a patient-support apparatus to not include a base. A patient-support apparatus in accordance with the present disclosure may include lift arms directly engaging a floor individually. Furthermore, lower ends of lift arms may be coupled together in various combinations prior to engaging a floor.

Motion drives 126 and 127 of lift mechanism 30 are illustratively shown to each include a cylinder housing 130 and a rod 132 extendable from a first end 136 of respective cylinder housings 130 as shown in FIG. 5. Methods for extending and retracting rod 132 from cylinder housing 130 can include use of a hydraulic actuator, an electronic actuator, or equivalents thereof, or other suitable methods. Cylinder housings 130 also have a second end 138 coupled to lower frame 70 of base 26. Rod 132 of motion drive 126 is coupled to motion coupler 128 of lift mechanism 30 and rod 132 of motion drive 127 is coupled to motion coupler 129 of lift mechanism 30.

In this example, motion coupler 128 and 129 of lift mechanism 30 each have a circular tube 142, and a pivot bracket 144, pivot bracket 144 being fixedly attached to circular tube 142. Circular tubes 142 each extend between two brackets 140 of base 26 and are rotatably coupled thereto. Brackets 140 are fixedly coupled to lower frame 70 of base 26. Lower ends 66 of lift arms 50 and 52 are fixedly attached to circular tube 142 of motion coupler 128 and lower ends 66 of lift arms 54 and 56 are fixedly attached to circular tube 142 of motion coupler 129.

Figure 6:
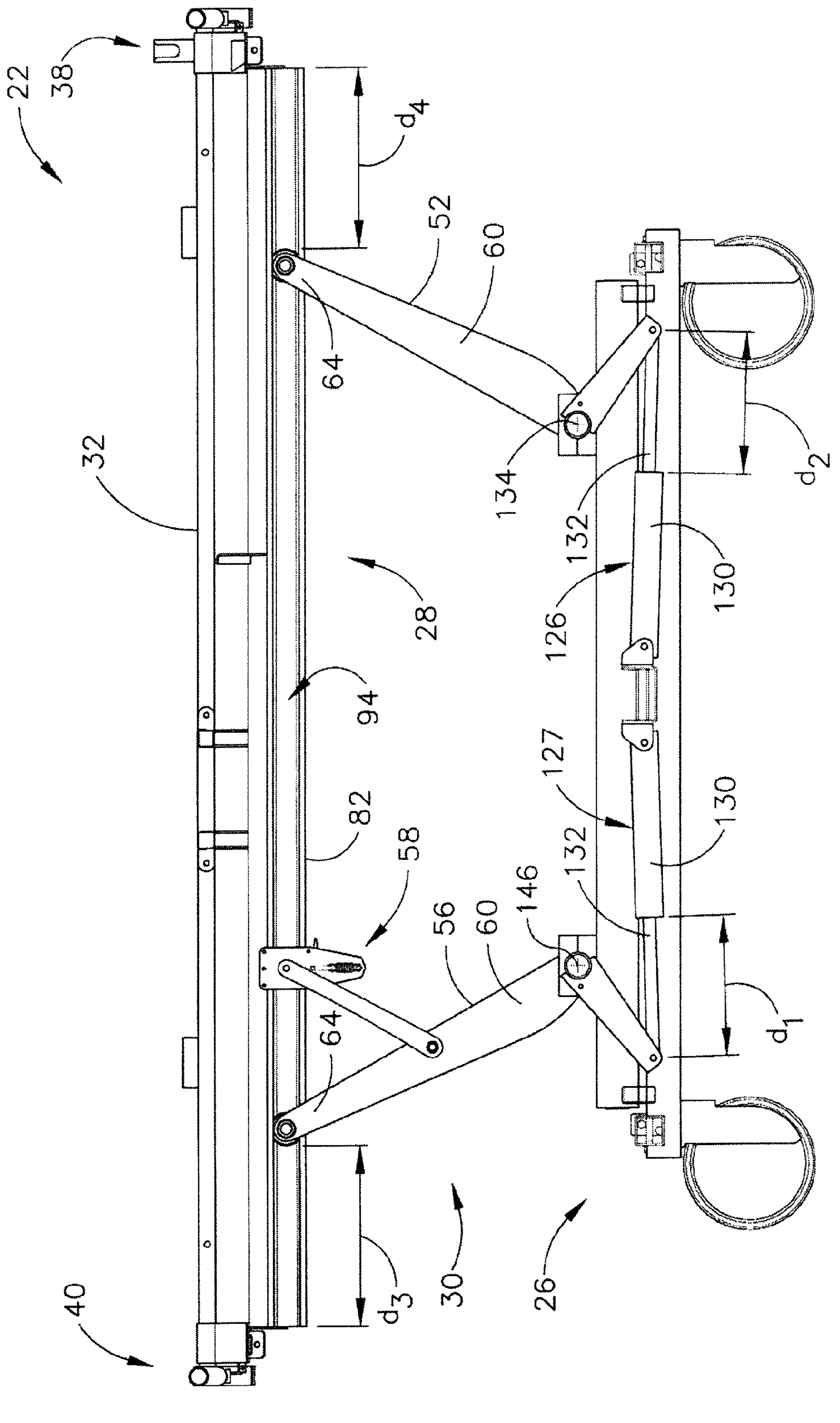
FIG. 6 is a sectional view of the patient-support apparatus of FIG. 1, taken along line 6-6 of FIG. 1, showing the lift mechanism in a raised position.

In this embodiment, pivot bracket 144 of motion coupler 128 is coupled to rod 132 of motion drive 126 so that as rod 132 of motion drive 126 extends from cylinder housing 130 of motion drive 126, pivot bracket 144 of motion coupler 128 rotates about axis 134 of FIG. 6. Thus, lift arms 50 and 52 rotate about axis 134. Likewise, pivot bracket 144 of motion coupler 129 is coupled to rod 132 of motion drive 127 so that as rod 132 of motion drive 127 extends from cylinder housing 130 of motion drive 127, pivot bracket 144 of motion coupler 129 rotates about an axis 146. Thus, lift arms 54 and 56 rotate about axis 146.

Lift arms 50-56 each have a slide assembly 110 coupled to upper end 64 of lift arms 50-56 in this example. Slide assembly 110 is illustratively shown in FIG. 5 having a roller 112 and post 114 with roller 112 pivotably coupled to a roller-end 116 of post 114 that allows pivoting of roller 112. Each post 114 goes through upper end 64 of lift arms 50-56, respectively. Each roller end 116 of posts 114 extends away from respective outward side 62 of lift arms 50-56, thus allowing roller 112 of slide assemblies 110 to rotate about a lateral axis adjacent to the respective outward side 62 of lift arms 50-56.

Slide assemblies 110 of lift arms 50 and 54 are slidably coupled to right rail member 80 and slide assemblies 110 of lift arms 52 and 56 are slidably coupled to left rail member 82. More specifically, openings 94 of right and left rail members 80, 82 are sized to receive post 114 of slide assembly 110 and grooves 98 of right and left rail members 80, 82 are sized to receive roller 112 of slide assembly 110, thus allowing roller 112 of slide assemblies 110 to slidably engage respective groove surfaces 96 of right and left rail members 80 and 82, as best shown in FIG. 5.

While slide assemblies 110 of lift arms 50-58 are shown to include a roller 112 and post 114, slide assemblies 110 may include other mechanisms for slidably coupling lift arms 50-54 to upper frame 28 of stretcher frame 22. For example, the slide mechanism may include surfaces that slide along the bottom of a rail member or a toothed wheel engaging a track in the upper frame.

Upper frame 28 is illustratively shown placed in a raised position above base 26 and the motion drives 126 and 127 of lift mechanism 30 are shown in the corresponding position in the sectional view of FIG. 6. Upper frame 28 is illustratively shown placed in a lowered position above base 26 and the motion drives 126 and 127 of lift mechanism 30 are shown in the corresponding position in the sectional view of FIG. 7. In this illustrative embodiment, as lift arms 50, 52 are moved between a raised position and a lowered position, upper ends 64 of lift arms 50, 52 move toward foot end 38 of patient-support apparatus 20 along right and left rail members 80, 82, respectively. Likewise, as lift arms 54, 56 are moved between a raised position to a lowered position, upper ends 64 of lift arms 54, 56 move toward head end 40 of stretcher frame 22 along right and left rail members 80, 82, respectively.

While upper ends 64 of lift arms 50, 52 move away from upper ends 64 of lift arms 54, 56 as head and foot ends 40, 38 concurrently move between a raised position to a lowered position, it is within the scope of the present disclosure for a lift mechanism of a patient-support apparatus to include two or more lift arms longitudinally spaced apart to move in a generally same direction when moving a frame. It is within the scope of the present disclosure for lift arms laterally spaced apart to move with substantially different motions while moving a frame between a raised position and a lowered position. Furthermore, a patient-support apparatus of the present disclosure may include only one lift arm.

Rod 132 of motion drive 127 is illustratively shown extended out of cylinder housing 130 of motion drive 127 a distance d1 and rod 132 of motion drive 126 is illustratively shown extended out of cylinder housing 130 of motion drive 126 a distance d2 in FIG. 6 when upper frame 28 of stretcher frame 22 is positioned in a raised position above the base 26. Rod 132 of motion drive 127 is illustratively shown extended out of cylinder housing 130 of motion drive 127 a distance d11 and rod 132 of motion drive 126 is illustratively shown extended out of cylinder housing 130 of motion drive 126 a distance d12 in FIG. 7 when upper frame 28 of stretcher frame 22 is positioned in a lowered position above base 26. In this embodiment, distance d11 is smaller when head end 40 of upper frame 28 is positioned in a lowered position above base 26 than distance d1 when head end 40 of upper frame 28 is positioned in a raised position above base 26. Likewise, distance d12 is smaller when foot end 38 of upper frame 28 is positioned in a lowered position above base 26 than distance d2 when foot end 38 of upper frame 28 is positioned in a raised position above base 26.

When rod 132 extends from cylinder housing 130 of motion drive 127, upper ends 64 of lift arms 54 and 56 pivot upward and downward with respect to base 26 about axis 146 and subsequently slide through right and left rail members 80 and 82, thereby raising head end 40 of stretcher frame 22 away from base 26 and lowering head end 40 toward base 26, respectively. Likewise, as rod 132 of motion drive 126 is extended and retracted from cylinder housing 130 of motion drive 126, upper ends 64 of lift arms 50 and 54 pivot upward and downward with respect to base 26 about axis 134 and subsequently slide through right and left rail members 80 and 82, thereby raising foot end 38 of stretcher frame 22 away from base 26 and lowering foot end 38 toward base 26, respectively.

Figure 7:
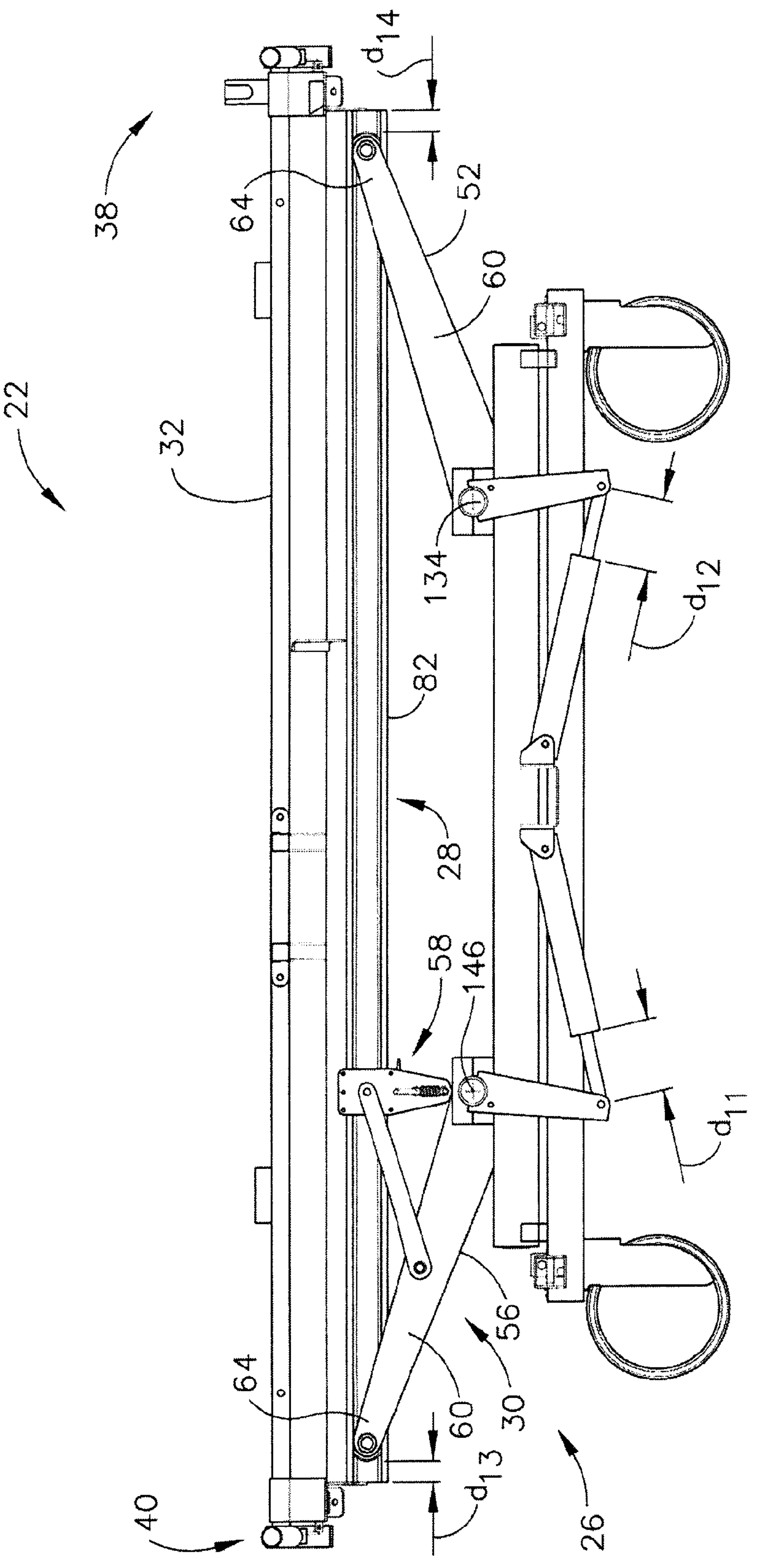
FIG. 7 is the sectional view similar to FIG. 6, but with the lift mechanism shown in a lowered position.

Furthermore, in this embodiment upper end 64 of lift arm 56 is positioned a distance d3 from the head end of left rail member 82 and upper end 64 of lift arm 52 is positioned a distance d4 from the foot end of left rail member 82 as shown in FIG. 6 when upper frame 28 is in the raised position. Upper end 64 of lift arm 56 is positioned a distance d13 from the head end of left rail member 82 and upper end 64 of lift arm 52 is positioned a distance d14 from the foot end of left rail member 82 as shown in FIG. 7 when upper frame 28 is in the lowered position. Distance d13 is smaller when the head end of upper frame 28 is positioned in a lowered position above base 26 than distance d3 when the head end of upper frame 28 is positioned in a raised position above base 26. Likewise, distance d14 is smaller when the foot end of upper frame 28 is positioned in a lowered position above base 26 than distance d4 when the foot end of upper frame 28 is positioned in a raised position above base 26.

When securing assembly 58 is in the secured position, as shown in the embodiments FIGS. 6, 7, the longitudinal position of upper frame 28 is generally maintained when upper frame 28 is moved between the raised position and the lowered position. When securing assembly 58 is in the release position as shown in FIGS. 3 and 4, the longitudinal position of upper frame 28 is not necessarily maintained when stretcher frame 22 is moved between the raised position and the lowered position.

With reference again to FIG. 5, moving lift arms 50 and 52 independently of lift arms 54 and 56 allows the stretcher frame 22 to be positioned into a tilt position with the head end of the upper frame 28 being lower than the foot end of the upper frame 28. Likewise, the stretcher frame 22 may be positioned in a reverse-tilt position with the head end of the upper frame 28 being higher than the foot end of the upper frame 28.

While lift mechanism 30 illustratively includes four lift arms 50-56, the frame 22 may include a lift mechanism with one or more lift arms positioned centrally upon base 26, around the perimeter of base 26, intermediate the perimeter and center portion of base 26, or combinations therein. Additionally, motion drives 126 and 127 and motion couplers 128 and 129 may be configured to allow either raising or lowering of upper frame 28 with respect to base 26 as rods 132 are extended from cylinder housing 130 of motion drives 126, 127.

Figure 8:
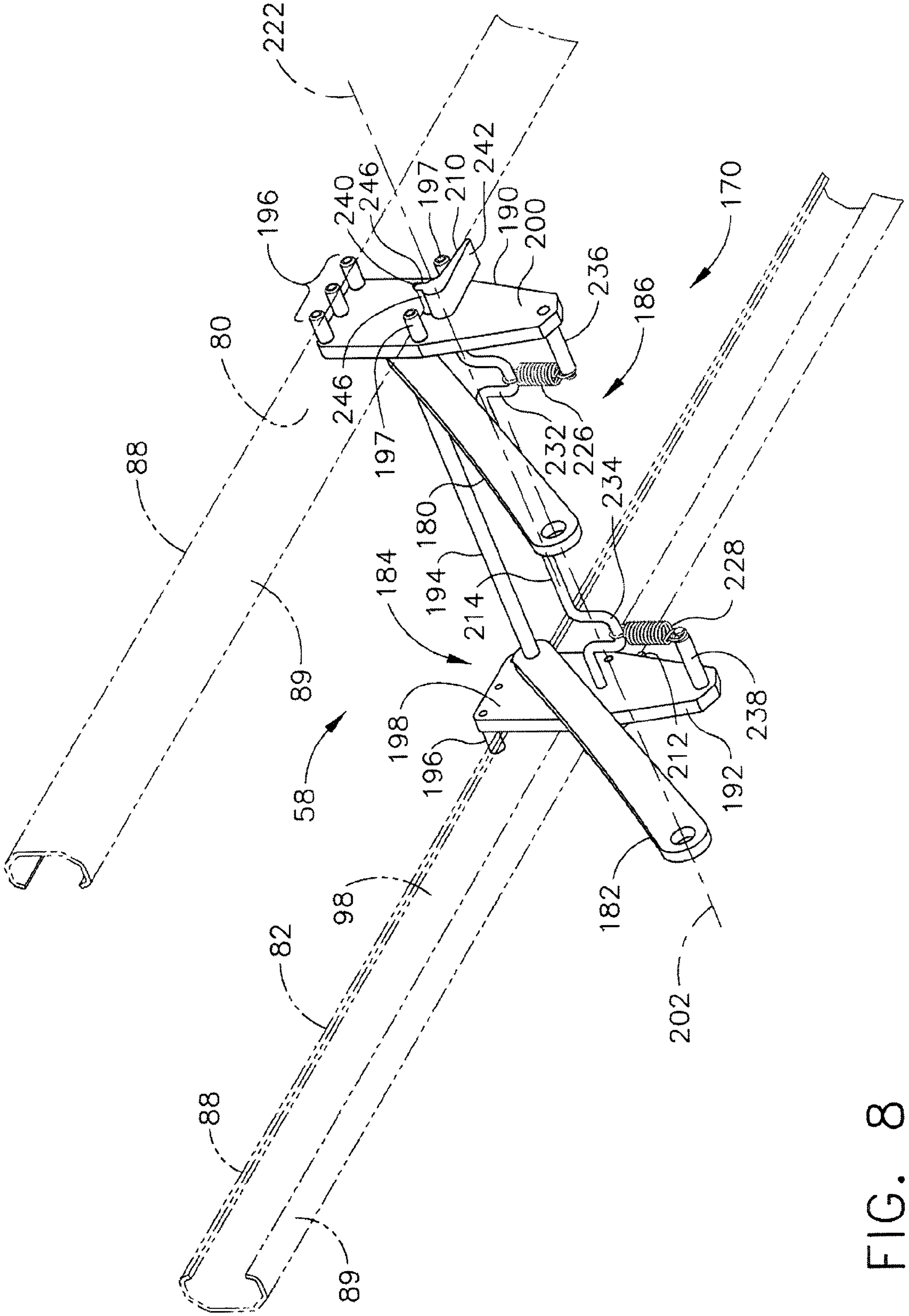
FIG. 8 is a perspective view of the securing mechanism of the patient-support apparatus of FIG. 1 shown in a secured position with a portion of the upper frame in phantom.
Figure 9:
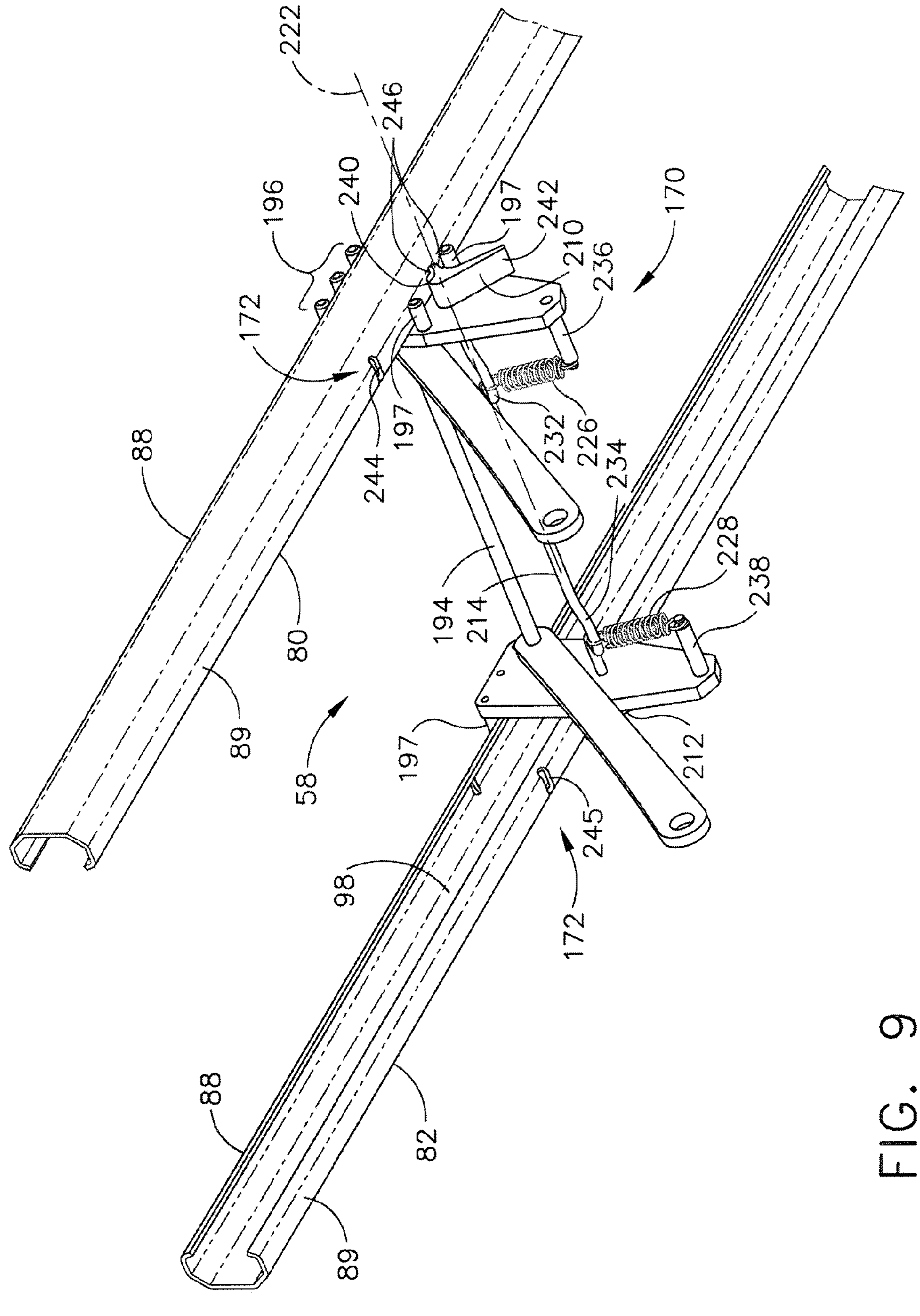
FIG. 9 is a perspective view, similar to FIG. 8, showing the securing mechanism in a released position with a latch situated outside a notch of the upper frame.

As was discussed above, the stretcher frame 22 of this embodiment includes securing assembly 58 having a secured position configured to retain the longitudinal position of upper frame 28 with respect to base 26 and a release position configured to allow adjustment of the longitudinal position of upper frame 28 with respect to base 26. Securing assembly 58 includes a latch member 170 and a catch member 172 as best shown in FIGS. 8-9. Latch member 170 includes a right link 180, a left link 182, structural assembly 184, and locking mechanism 186. Securing assembly 58 is shown in a secured position in FIG. 8 and is shown in a released position in FIG. 9.

Structural assembly 184 of latch member 170 has a right structural plate 190 and a left structural plate 192 with a pivot rod 194 extending therebetween, in this example. Right structural plate 190 and a left structural plate 192 each have an inward side 198 and an outward side 200. Outward sides 200 of structural plates 190 and 192 are adjacent to right and left rail members 80 and 82, respectively. Structural assembly 184 also has three top rollers 196 and three bottom rollers 197 rotatably coupled to and extending outward from outward side 200 of structural plate 190, and three top rollers 196 and three bottom rollers 197 rotatably coupled to and extending outward from outward side 200 of structural plate 192. Top and bottom rollers 196, 197 are spaced apart on structural plates 190 and 192 such that top rollers 196 slidably engage top side 88 of right and left rail members 80 and 82 and bottom roller 197 slidably engage bottom side 89 of right and left rail members 80 and 82.

With reference to FIGS. 5-9, in this embodiment, right link 180 of latch member 170 extends between and is pivotably coupled to lift arm 54 and pivot rod 194. Likewise, left link 182 of latch member 170 extends between and is pivotably coupled to lift arm 56 and pivot rod 194. When stretcher frame 22 is moved from a raised position to a lowered position as discussed above, right link 180 and left link 182 pivot about axis 202. When securing assembly 58 is in the released position, as will be described in further detail below, the coupling of links 180 and 184 to lift arms 54, 56 and structural assembly 184 allow latch member 170 to slide along top side 88 and bottom side 89 of rail members 80, 82 concurrently with the sliding of lift arms 54 and 56 within groove 98 of rail members 80 and 82.

Locking mechanism 186 of latch member 170 has a right latch 210, a left latch 212 and a bias rod 214 extending therebetween in this embodiment illustrated in FIG. 8. Bias rod 214 has a right end (not shown) extending through right structural plate 190 of structural assembly 184 and outward from outward side 200 of right structural plate 190. The right end of bias rod 214 is fixedly engaged with right latch 210. Likewise, bias rod 214 has a left end (not shown) extending through left structural plate 192 of structural assembly 184 and outward from outward side 200 of left structural plate 192. The left end of bias rod 214 is fixedly engaged with left latch 212 (which is the same as right latch 210). As right latch 210 is pivoted about axis 222, bias rod 214 pivots about axis 222 and therefore left latch 212 pivots about axis 222.

Bias rod 214 has a right bend portion 232 and a left bend portion 234 intermediate right and left structural plates 190 and 192 in this example, as best shown in FIGS. 8-9. Right bend portion 232 and left bend portion 234 generally extend away from axis 222 the same length and generally extend away from axis 222 in the same plane. Locking mechanism 186 has a right bias spring 226 extending between right bend portion 232 of bias rod 214 and a spring-engagement member 238 of structural assembly 184. Spring engagement member 238 is attached to and extends away from inward side 198 of right structural plate 190.

Locking mechanism 186 of this embodiment also has a left bias spring 228 extending between left bend portion 234 of bias rod 214 and a spring-engagement member 238 of structural assembly 184. Spring engagement member 238 is attached to and extends away from inward side 198 of left structural plate 192. Bias springs 226 and 228 are sized such when bias springs 226 and 228 are allowed to compress, right bend portion 232 is pulled toward spring engagement member 236 and left bend portion 234 is pulled toward spring engagement member 238. While locking mechanism 186 is illustratively shown to include two bias springs 226 and 228, locking mechanism 186 may have one bias spring in some embodiments. Other mechanisms could be used also.

Right latch 210 of locking mechanism 186 has a stop portion 240 and a release portion 242, where stop portion 240 has two stop surfaces 246 that are receivable by catch member 172 of securing assembly 58, in this embodiment, as best shown in FIG. 9. Likewise, left latch 212 of locking mechanism 186 has a stop portion (not seen) and a release portion (not seen), where the stop portion of left latch 212 has two stop surfaces (not seen) that are receivable by catch member 172.

In this embodiment, catch member 172 is integrally formed in upper frame 28 in the embodiment of FIG. 9. More specifically, catch member 172 includes a first notch 244 formed in bottom side 89 of right rail member 80 and a second notch 245 formed in bottom side 89 of left rail member 82. First notch 244 of catch member 172 is sized to receive stop portions 240 of right latch 210 and second notch 245 of catch member 172 is sized to receive the stop portions of left latch 212. Locking mechanism 186 is configured so that stop portion 240 of right latch 210 is received within first notch 244 of catch member 172 concurrently with the stop portion of left latch 212 being received within second notch 245 of catch member 172. Additionally, locking mechanism 186 is configured so that stop portion 240 of right latch 210 and the stop portion of left latch 212 are receivable by notches 244 and 245 of catch member 172, respectively, when right bend portion 232 of bias rod 214 is pulled toward spring engagement member 236 of structural assembly 184 and left bend portion 234 of bias rod 214 is pulled toward spring engagement member 238 of structural assembly 184 and stop portion 240 of right latch 210 is aligned with first notch 244 of catch member 172 and the stop portion of left latch 212 is aligned with second notch 245 of catch member 172.

When the longitudinal position of upper frame 28 is adjusted with respect to base 26, such that stop portion 240 of right latch 210 is positioned over first notch 244 of catch member 172 and the stop portion of left latch 212 is positioned over second notch 245 of catch member 172, bias springs 226 and 228 rotate bias rod 214 such that stop surfaces 246 of stop portion 240 of right latch 210 engage first notch 244 of catch member 172 and the stop surfaces of the stop portion of left latch 212 engage second notch 245 of catch member 172. Therefore, securing assembly 58 is placed into the secured position, as shown best in FIG. 8. Furthermore, when secured member 58 is in the secured position, secured member 58 maintains a longitudinal position of upper frame 28 with respect to base 26, as shown best in FIGS. 6 and 7. (e.g. the upper frame 28 is prevented from moving in the direction 48 shown in FIG. 4, relative to base 26)

In this example of FIG. 8, release portion 242 of right latch 210 is sized to allow a caregiver to press upon release portion 242 with their fingertips thereby pivoting release portion 242 about axis 222 and subsequently releasing stop portion 240 from within first notch 244 of catch member 172. The right bias spring 226 is further extended when stop portion 240 of right latches 210 is no longer received by first notch 244 of catch member 172. Likewise, the release portion of left latch 212 is sized to allow a caregiver to press upon the release portion with their fingertips thereby pivoting the release portion of left latch 212 about axis 222 and subsequently releasing the stop portion of left latch 212 from within second notch 245 of catch member 172, as illustratively shown in FIG. 9. The left bias spring 228 is further extended when the stop portion of left latches 212 is no longer received by second notch 245 of catch member 172.

When stop portion 240 of right latch 210 is no longer received by first notch 244 of catch member 172 and the stop portion of left latch 212 is no longer received by second notch 245 of catch member 172, securing assembly 58 of this example is in the released position, as shown best in FIG. 9. As explained above, when securing assembly 58 is in the released position, latch member 170 and lift arms 50-56 may slide along rail members 80 and 82 thereby allowing longitudinal adjustment of upper frame 28 with respect to base 26 in the direction 48, as shown in FIGS. 2-4.

A caregiver may wish to use the example fluoroscopic imaging machine 150 shown in FIG. 2 in combination with the head end of patient-support apparatus 20. With reference to FIGS. 1-9, the caregiver may press downward on release portion 242 of right latch 210 or the release portion of left latch 212, perhaps selected by choosing the side the caregiver is standing on. When latch member 170 of securing assembly 58 is disengaged from catch member 172 of securing assembly 58, securing assembly 58 is in the released position, thus allowing the caregiver to slide the upper frame 28 toward head end 40 of patient-support apparatus 20. The caregiver may then choose to position fluoroscopic imaging machine 150 in closer proximity to the head end of the stretcher frame due to the additional open space now available below the head-end and the clearance from base 26.

A lock may be configured to automatically move into a locked position when a lift arm or a member of the lock is positioned at a predetermined location on the stretcher frame, such as the location of catch member 172 integrally appended with upper frame 28. Locations for a lock to be engaged may include positions adjacent the head end, the foot end, and intermediate the head end and foot end. Additionally, a lock may be configured to engage either the upper frame or the base anywhere between the head end and the foot end of the frame.

While the illustrative embodiment included latch member 170 of securing assembly 58 having two links 180, 182, it is within the scope of the present disclosure for one link to be provided on either the left or right side, or multiple links may be provided. Additionally, it is within the scope of the present disclosure for securing assembly 58 to be located at foot end 38 of stretcher frame 22.

While securing assembly 58 includes latch member 170 and catch member 172, it is within the scope of the present disclosure for a lock to include catch coupled to a lift arm, a link, or upper frame. A lock may include a latch coupled to a lift arm, a link, or upper frame. Additionally, a lock may include only a catch, or a latch, or a combination of one or more of each.

Figure 10:
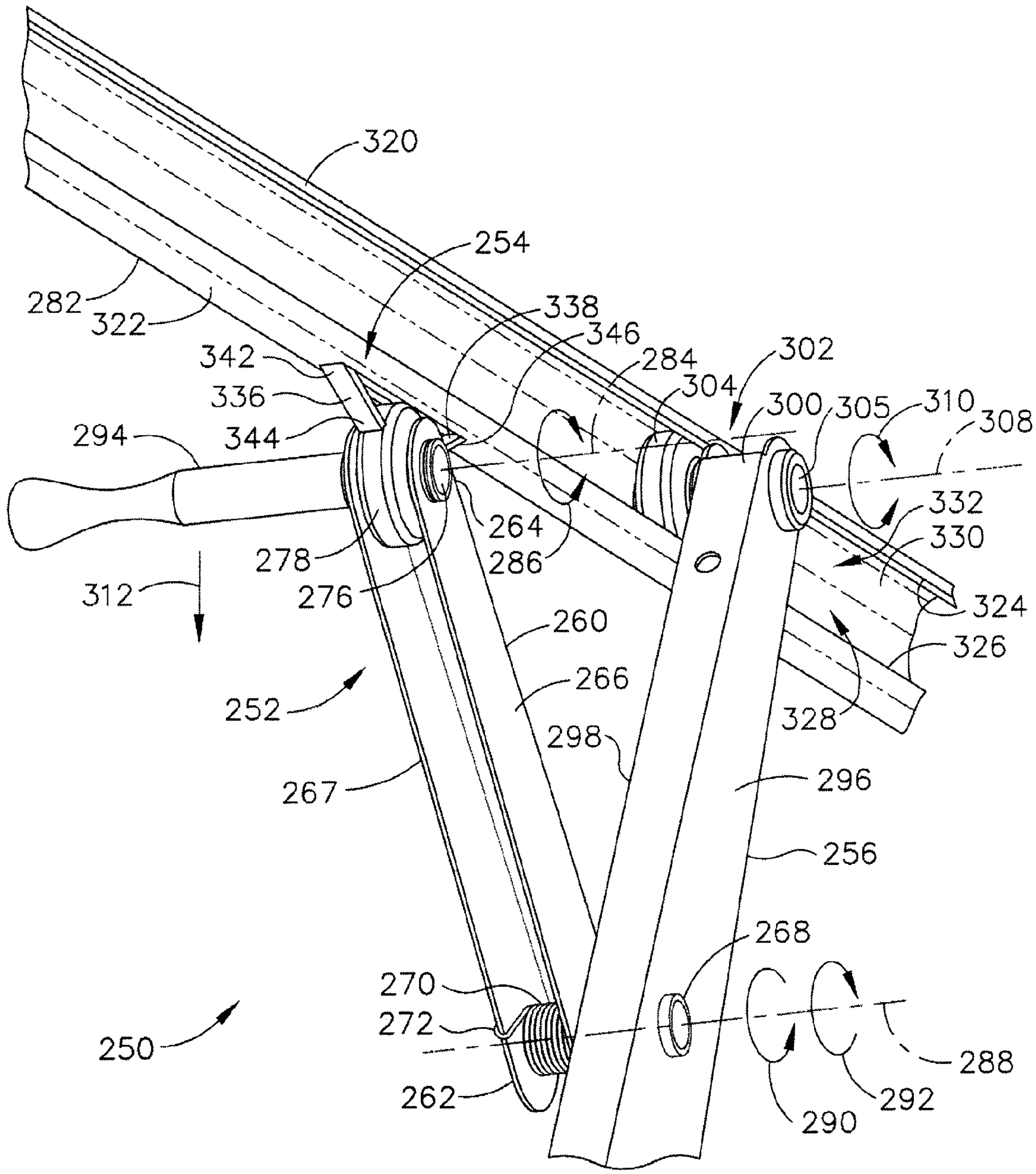
FIG. 10 is a perspective view of another illustrative embodiment of a securing mechanism, shown in a secured position with a portion of the upper frame.

Another embodiment is illustrated in FIG. 10. In this embodiment, a securing assembly 250 is shown in a secured position on a stretcher frame such as, for example, stretcher frame 22 in FIG. 1. The illustrative stretcher frame includes a lift arm 256 and an upper frame with a left rail member 282. Lift arm 256 includes an inward side 296, an outward side 298, an upper end 300, and a slide assembly 302 coupled to upper end 300 of lift arm 256, as shown in FIG. 10. Slide assembly 302 has a post 305 coupled to lift arm 256 and extending therethrough and away from outward side 298 of lift arm 256. Slide assembly 302 of this embodiment also has a roller 304 rotatably coupled to post 305 allowing roller 304 to rotate about axis 308 in directions indicated by arrow 310.

Left rail member 282 of this embodiment of FIG. 10 has an inward side 320 facing toward the longitudinal center of the stretcher frame and a bottom side 322. Inward side 320 is formed to include two edges 324, 326 extending the length of rail member 282. Edges 324, 326 form an opening 328 that, in cooperation with a groove surface 330 extending between edges 324, 326, defines a groove 332.

Slide assembly 302 of lift arm 256 is slidably coupled to left rail member 282. More specifically, in this example, opening 328 of left rail member 282 is sized to receive post 305 of slide assembly 302 and groove 332 of left rail member 282 is sized to receive roller 304 of slide assembly 302 thus allowing roller 304 to slidably engage groove surface 330 of left rail member 282.

Securing assembly 250 of this embodiment includes latch member 252 and a catch member 254. Latch member 252 includes a link 260 having a pivot end 262, a slide end 264, an inward portion 266, and an outward portion 267 spaced apart therefrom. Latch member 252 of securing assembly 250 also includes a spring post 268 coupled to a lift arm 256 and rotatably coupled to pivot end 262 of link 260 and extending therethrough. Link 260 pivots about axis 288 in directions indicated by arrows 290 and 292. A torsion spring 270 of latch member 252 is axially centered over spring post 268 in this embodiment. A first end (not shown) of torsion spring 270 is coupled to spring post 268 and a second end 272 of torsion spring 270 is coupled to outward portion 267 of link 260, thereby biasing link 260 to rotate in a direction indicated by arrow 292.

Latch member 252 of securing assembly 250 of this embodiment also includes a roller post 276 coupled to slide end 264 of link 260 and extending between outward portion 267 and inward portion 266. A roller 278 of latch member 252 is axially centered over and is rotatably coupled to roller post 276 thereby allowing roller 278 to rotate about axis 284 in directions indicated by arrow 286. Latch member 252 further includes a handle 294 coupled to slide end 264 of link 260 extending away from outward portion 267 of link 260.

Second end 272 of torsion spring 270 is coupled to outward portion 267 of link 260 in this embodiment of FIG. 10. Accordingly, torsion spring 270 applies a spring force in the direction indicated by arrow 292, thereby engaging roller 278 of latch member 252 with bottom side 322 of rail member 282 when no external force is applied to handle 294 of latch member 252 or any other portion of latch member 252. When a force is applied by the caregiver in a direction indicated by arrow 312 to handle 294 sufficient to overcome the spring force applied to link 260 by torsion spring 270, link 260 and second end 272 of torsion spring 270 will rotate in a direction indicated by arrow 290, thereby disengaging roller 278 from bottom side 322 of rail member 282.

Catch member 254 of the embodiment of securing assembly 250 in FIG. 10 is illustratively shown as integrally formed in rail member 282. More specifically, catch member 254 is formed by a first stop tab 336 and a second stop tab 338 extending from and integrally formed with bottom side 322. Stop tabs 336 and 338 are illustratively shown as formed on bottom side 322 of rail member 282. First stop tab 336 has a joined end 342 appended to bottom side 322 of rail member 282 and a free end 344 spaced apart from joined end 342 such that an acute angle is formed between a line along rail member 282 in the longitudinal direction and a line including joined end 342 and free end 344. Likewise second stop tab 338 has a joined end 346 appended to bottom side 322 of rail member 282 and a free end (not shown) spaced apart from joined end 346 such that an acute angle is formed between a line along rail member 282 in the longitudinal direction and a line including joined end 346 of stop tab 338 and the free end of stop tab 338. Free end 344 of stop tab 336 is spaced apart from the free end of stop tab 338 sufficiently to allow roller 278 of latch member 252 to engage both free end 344 of stop tab 336 and the free end of stop tab 338 when roller 278 is placed between stop tab 336 and stop tab 338.

A caregiver may wish to use a C-Arm X-Ray diagnostic equipment or other equipment in combination with the head end of a stretcher frame that includes the example of the left rail member 282, lift arm 256 and securing assembly 250. The caregiver may begin by downwardly applying a force upon handle 294 of latch member 252 of securing assembly 250 sufficient to disengage latch member 252 from catch member 254, in the direction 312. When latch member 252 of securing assembly 250 is disengaged from catch member 254, the caregiver may choose to slide the upper frame of the stretcher frame longitudinally toward the head end of the stretcher thereby allowing the caregiver to position the equipment in closer proximity to the head end of the stretcher frame, such as in the manner shown in the embodiment of FIG. 3 (as compared to FIG. 6).

While latch member 252 of securing assembly 250 in FIG. 10 illustratively includes roller 278 slidably engaging bottom side 322 of left rail member 282, many other configurations and embodiments are possible. For example, a latch member may be used that includes a link with an end slidably coupled to groove 332 of rail member 282. Other configurations of the latch to provide frictional engagement of securement may be used as well. Additionally, a securing assembly may be used that includes a latch coupled to a link that is detachable from either upper frame 28 or lift mechanism 30.

Although certain illustrative embodiments have been described in detail above, many embodiments, variations and modifications are possible that are still within the scope and spirit of this disclosure as described herein and as defined in the following claims.

The invention claimed is:

1. A patient-support apparatus comprising:

a base, a frame having a head end, a foot end spaced apart from the head end in a longitudinal direction, a first lift arm coupled to the base and the frame, wherein the first lift arm is pivotable relative to the base to raise and lower at least a portion of the frame relative to the base, and a securing assembly including a latch, the securing assembly being configurable into a locked configuration and an unlocked configuration, the frame being manually positionable relative to the base in the longitudinal direction between a first position and a second position when the securing assembly is in the unlocked configuration, and the frame being prevented from moving in the longitudinal direction relative to the base when (i) the frame is in the first position or the second position and (ii) the securing assembly is in the locked configuration.

2. The patient-support apparatus of claim 1, wherein the frame is coupled to a radiolucent support deck.

3. A patient-support apparatus comprising:

a base, a frame having a head end, a foot end spaced apart from the head end in a longitudinal direction, a first lift arm coupled to the base and the frame, wherein the first lift arm is pivotable relative to the base to raise and lower at least a portion of the frame relative to the base, and a securing assembly including a latch, the securing assembly being configurable into a locked configuration and an unlocked configuration, the frame being manually positionable relative to the base in the longitudinal direction when the securing assembly is in the unlocked configuration, and the frame being prevented from moving in the longitudinal direction relative to the base when the securing assembly is in the locked configuration, wherein the first lift arm is coupled to the frame at a first end and the first end of the first lift arm moves along the frame when the frame is raised relative to the base.

4. The patient-support apparatus of claim 3, wherein the first end of the first lift arm includes a first roller.

5. A patient-support apparatus comprising:

a base, a frame having a head end, a foot end spaced apart from the head end in a longitudinal direction, a first lift arm coupled to the base and the frame, wherein the first lift arm is pivotable relative to the base to raise and lower at least a portion of the frame relative to the base, and a securing assembly including a latch, the securing assembly being configurable into a locked configuration and an unlocked configuration, the frame being manually positionable relative to the base in the longitudinal direction when the securing assembly is in the unlocked configuration, and the frame being prevented from moving in the longitudinal direction relative to the base when the securing assembly is in the locked configuration, wherein the securing assembly includes a link rotatably coupled at a first end to the lift arm and the frame including at least one catch engaging the latch when the securing assembly is in the locked configuration.

6. A patient-support apparatus comprising:

a base, a frame having a head end, a foot end spaced apart from the head end in a longitudinal direction, a first lift arm coupled to the base and the frame, wherein the first lift arm is pivotable relative to the base to raise and lower at least a portion of the frame relative to the base, and a securing assembly including a latch, the securing assembly being configurable into a locked configuration and an unlocked configuration, the frame being manually positionable relative to the base in the longitudinal direction when the securing assembly is in the unlocked configuration, and the frame being prevented from moving in the longitudinal direction relative to the base when the securing assembly is in the locked configuration, wherein the patient support apparatus further comprises a second lift arm coupled to the base and the frame, wherein the second lift arm is pivotable relative to the base to raise and lower at least a portion of the frame relative to the base, and wherein the second lift arm is coupled to the frame at a first end and the first end of the second lift arm moves along the frame when the frame is raised relative to the base.

7. The patient-support apparatus of claim 6, wherein the first lift arm is pivotable relative to the base to raise and lower the head end of the frame and the second lift arm is pivotable relative to the base to raise and lower the foot end of the frame.

8. The patient-support apparatus of claim 6, wherein the securing assembly is in a locked configuration during the raising and lowering of the frame relative to the base.

9. The patient-support apparatus of claim 8, wherein the frame includes a right rail member comprising a groove configured to slideably engage with the first roller.

10. A patient-support apparatus comprising:

a base, a frame having a head end, a foot end spaced apart from the head end in a longitudinal direction, the frame including a right rail member and a left rail member, the frame being manually positionable relative to the base in the longitudinal direction, and a securing assembly comprising a left latch lockably engaging the left rail member and a right latch lockably engaging the right rail member when the securing assembly is in a locked configuration and the left latch slidably engaging the left rail member and the right latch slidably engaging the right rail member when the securing assembly is in an unlocked configuration, wherein the left latch includes a left release portion configured to release the lockable engagement of both the left latch with the left rail member and the right latch with the right rail member and wherein the right latch includes a right release portion configured to release the lockable engagement of both the left latch with the left rail member and the right latch with the right rail member.

11. The patient-support apparatus of claim 10, wherein the securing assembly includes at least one spring biasing the securing assembly toward a locked configuration.

12. The patient-support apparatus of claim 11, wherein the right rail member includes catches configured to lockably engage the right latch when the right latch is aligned with a catch.

13. The patient-support apparatus of claim 12, wherein the left rail member includes catches configured to lockably engage the left latch when the left latch is aligned with a catch.

14. The patient-support apparatus of claim 13, wherein the left rail catches and right rail catches are configured to lockably engage both the left latch and right latch at predetermined longitudinal positions of the frame in relation to the base.

15. The patient support apparatus of claim 10, wherein the left latch includes a release portion configured to release the lockable engagement of both the left latch with the left rail member and the right latch with the right rail member.

16. The patient-support apparatus of claim 15, wherein the securing assembly includes a bias rod coupled to both the left latch and the right latch biasing both the left latch and the right latch to a locked configuration.

17. The patient-support apparatus of claim 10, wherein the bias rod includes a left bend portion and a right bend portion.

18. The patient-support apparatus of claim 10, wherein the securing assembly includes rollers configured to engage opposing outer surfaces of the right rail member and opposing outer surfaces of the left rail member.

19. A patient-support apparatus comprising:

a base, a frame having a head end, a foot end spaced apart from the head end in a longitudinal direction, and a side rail member including at least one complementary pair of stop tab catches, and a securing assembly including a latch comprising a roller configured to engage at least one stop tab catch, and a handle, the frame being positionable relative to the base in the longitudinal direction when the roller is disengaged from the at least one stop tab catch.

20. The patient-support apparatus of claim 19, wherein the latch further comprises a spring configured to bias the roller to contact the side rail and the handle is configured to overcome the spring biasing the roller toward contact with the side rail member when actuated.

21. The patient-support apparatus of claim 19, wherein the complementary pair of stop tab catches comprises a first stop tab joined at a first end to the side rail and including a second end spaced apart from the side rail forming an acute angle with the side rail, and a second stop tab joined at a first end to the side rail and including a second end spaced apart from the side rail forming an acute angle with the side rail.

22. The patient-support apparatus of claim 21, wherein the second end of the first tab is spaced apart from the second end of the second tab a first distance and the first end of the first tab is spaced apart from the first end of the second tab a second distance, and the first distance being smaller than the second distance.

23. The patient-support apparatus of claim 21, wherein the roller engages an outer surface of the side rail, and the first distance between the second end of the first tab and the second end of the second tab is configured to allow the roller to engage both the second end of the first tab and the second end of the second tab when the securing assembly is in a locked configuration.

* * * * *